United States Patent [19]

Malins

[11] Patent Number: 5,601,981
[45] Date of Patent: Feb. 11, 1997

[54] METHODS FOR DETERMINING AND AGENTS FOR MODULATING CELLULAR REDOX POTENTIAL AND GENOTOXIC STATES

[75] Inventor: Donald C. Malins, Seattle, Wash.

[73] Assignee: Pacific Northwest Research Foundation, Seattle, Wash.

[21] Appl. No.: 319,251

[22] Filed: Oct. 6, 1994

Related U.S. Application Data

[63] Continuation of Ser. No. 55,818, Apr. 30, 1993, abandoned.

[51] Int. Cl.[6] ............................ C12Q 1/68; A61K 48/00
[52] U.S. Cl. ........................... 435/6; 435/5; 435/7.2; 435/25; 435/26; 435/27; 435/28; 435/29; 435/69.1; 435/70.1; 435/71.1; 435/132; 435/172.3; 435/262; 435/267; 435/810; 436/501; 436/63; 514/44; 935/77; 935/78
[58] Field of Search .................. 435/5, 6, 810, 435/7, 2, 25, 26, 27, 28, 29, 69.1, 70.1, 71.1, 132, 172.3, 262, 267; 436/501, 63; 514/44; 935/77, 78

[56] References Cited

U.S. PATENT DOCUMENTS

| | | | |
|---|---|---|---|
| 5,043,165 | 8/1991 | Radhakrishnan | 424/450 |
| 5,196,510 | 3/1993 | Rodwell et al. | 530/324 |
| 5,198,336 | 3/1993 | Knobeloch et al. | 435/4 |
| 5,246,707 | 9/1993 | Haynes | 424/450 |

OTHER PUBLICATIONS

Steenken; *Purine Bases, Nucleasides, and Nucleotides...*; Chem Rev 1989, vol. 89, pp. 503–520.

Floyd; *The Role of 8–Hydroxyguanine*...; Table 1; Carcinogenesis 1990, vol. II, pp. 1447–1449.

Troll & Wiesner; *The Role of Oxygen Radicals*...; Ann Rev Pharmacol Toxicol 1985, vol. 25; pp. 509–528.

Malins & Haimanot; *Major Alterations in the Nucleotide Structure of DNA*... Cancer Res 1991, vol. 51, 5430–5432.

Malins & Haimanot; *The Etiology of Cancer: Hydroxyl Radical–Induced DNA Lesions*... Aquatic Toxicol '91, vol. 20, 7 pages.

Lim, Frenkel & Troll; *Tamoxifen Suppresses Tumor Promoter–induced Hydrogen Peroxide*... Cancer Res., '92/vol. 52, 4969–4972.

*Primary Examiner*—Ardin H. Marschel
*Attorney, Agent, or Firm*—Stephen M. Evans; David L. Garrison

[57] ABSTRACT

Methods for determining the genotoxic or carcinogenic status of a subject by analyzing the cellular redox potential of a test specimen where an increased risk of, or presence of, genotoxic injury or cancer is indicated when the cellular redox potential favors oxidatively derived modified nucleotide bases. A sensitive method is disclosed wherein DNA is isolated from a test specimen obtained from a test subject and assayed for modified nucleotide bases that have formed either stable reductively formed derivatives or stable oxidatively formed derivatives. By identifying and comparing those modified nucleotide bases derived via reductive pathways to those modified nucleotide bases derived via oxidative pathways, a determination as to the cancer status of the test specimen can be made wherein a greater cancerous state exists when the ratio between the two species of modified nucleotide bases indicates that oxidatively formed derivative are favored over reductively formed derivatives. Also disclosed are methods for modulating the cellular redox potential so as to decrease the likelihood of oxidatively derived modified base formation and cancer formation. Methods for monitoring the efficacy of such therapy are additionally disclosed.

16 Claims, 6 Drawing Sheets

FIG.10
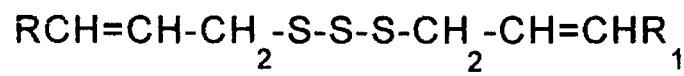
Diallyl trisulfides
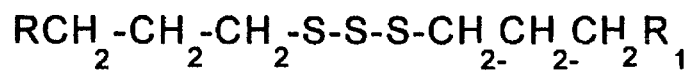
Trisulfides
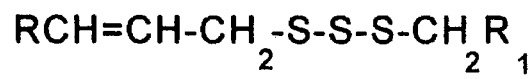
Allyl trisulfides
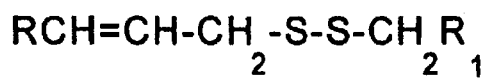
Allyl disulfides
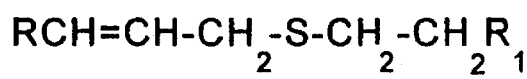
Diallyl sulfides
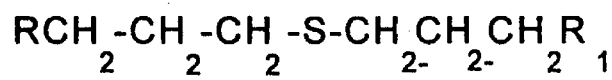
Disulfides

METHODS FOR DETERMINING AND AGENTS FOR MODULATING CELLULAR REDOX POTENTIAL AND GENOTOXIC STATES

This invention was made with government support under Grant Number DAMD17-92-J-2006 sponsored by the United States Army Corps of Engineers Environmental Quality Research and Development Program through the United States Army Medical Research and Development Command. The government has certain rights in the invention.

This application is a continuation of U.S. patent application Ser. No. 08/055,818, filed Apr. 30, 1993, now abandoned.

FIELD OF THE INVENTION

The present invention relates generally to diagnostic and prognostic methods for assessing the cancer status of a subject and methods for modifying that status. More particularly, the invention provides methods for determining the cancer status (healthy, precancerous, or cancerous) of a subject by analyzing the cellular redox potential as it affects cellular DNA and provides methods for modulating the cellular redox potential so as to affect cancer formation.

BACKGROUND OF THE INVENTION

The mechanism generally responsible for cellular replication is DNA transcription whereby genetic information about an organism as embodied in the DNA is transferred to each subsequently formed cell. It is during this replicating process that errors in the genetic code, in the form of miscoding or base pair errors (base lesions), may be passed from one cell to further generations. Some such lesions, or groups thereof, are detrimental and may result in death of the organism or neoplasia. Other lesions may have little detectable effect or may be readily repaired by enzymes produced by or introduced into the organism. Still other base lesions are beneficial and promote diversity and adaptation. It is the first category which is of great interest to the human population.

Because destruction or alteration of DNA sequences can have catastrophic consequences, e.g. cancer, much research has been conducted into identifying why and how such alterations take place. It has been shown that exposure to high levels of radiation or oxidizing chemicals causes destruction of DNA to varying degrees. For example, it has been shown that DNA misreplication occurred when bacteria was exposed in vitro to high levels of radiation so as to cause oxidatively modified nucleotide base lesions to appear. As a consequence of this and other research, it has been proposed that a primary promoter of DNA misreplication is the formation of oxidatively modified nucleotide bases. Experiments conducted by the inventor have extended this concept to show that such modifications to DNA actually occurred in vivo. Thus, it has been established that exposure to oxidative molecules in general and oxygen radicals in particular induced DNA lesions in the form of oxidatively modified nucleotide bases, and that these lesions were linked to carcinogenesis.

Further experiments conducted by the inventor have shown that exposure to known environmental toxins also caused oxidatively modified nucleotide bases to appear in vivo. In these further experiments, feral fish were taken from an environment known to contain carcinogenic compounds. Assays were conducted for DNA lesions and the resulting data showed that high levels of certain oxidatively modified nucleotide bases were present in cancerous tissues. The data indicated that cancerous tissues contained abnormally high levels of modified purine bases: 4,6-diamino-5-formamidopyrimidine (Fapy-A) and 2,6-diamino-4-hydroxy-5-formamidopyrimidine (Fapy-G), and 8-hydroxyguanine (8-OH-Gua) and 8-hydroxyadenine (8-OH-Ade). From this research, the initiator of these modifications was identified—the hydroxyl radical (.OH).

From the foregoing findings, a determination of a cancerous or precancerous state could be made by assaying for elevated concentration levels of the aforementioned oxidatively modified nucleotide bases. This discovery is the subject of pending U.S. patent application Ser. No. 07/806,487 which is incorporated herein by reference. The significance of this discovery is that for the first time, it was shown that a broad-based indicator of a cancerous state or elevated cancer risk could be utilized by conducting an assay for abnormally high concentration levels of oxidatively modified nucleotide bases. Moreover, by identifying the .OH radical as the molecule responsible for most oxidative modifications of DNA which produced genotoxic lesions, treatments could be carried out to reduce or eliminate its presence, thereby decreasing the risk of cancer or possibly arresting its continuation.

However, the data providing the association between the presence of oxidatively modified nucleotide bases and cancer raised some new questions. For example, some feral fish obtained from a tumor bearing population were found to have elevated concentrations of the identified oxidatively modified nucleotide bases, but these fish did not exhibit tumorigenesis. While the evidence indicated that these fish were at an increased risk of tumorigenesis as compared to a normal, non-tumor bearing population, the fact remained that these fish did not exhibit tumor formation. In other words, the degree of risk was not known and the reason for the cancer non-expression was not apparent.

It is well known that certain organisms exhibit tumorigenesis even though they are not exposed to environmental influences that promote cancerous growth. A potential explanation for this phenomenon is that in aerobic eukaryotic cells, molecular oxygen is reduced and yields, in minor but detectable quantities, toxic oxygen intermediates. The intermediates are generally superoxide anions ($O_2^-$.) and hydrogen peroxide ($H_2O_2$) which are considered undesirable, but not in and of themselves especially deleterious, and hydroxyl radicals (.OH) and singlet oxygen ($O_2\uparrow$) which are extremely reactive and toxic to most molecules in living cells. While $O_2^-$. and $H_2O_2$ are not intrinsically as toxic as .OH and $O_2\uparrow$, additional metabolic processes cause the formation of the more damaging variety: $O_2^-.+H_2O_2 \rightarrow .OH+OH^-+O_2$. And while this reaction proceeds at a generally slow pace, metal ions such as Fe (II) that are present in most biological organisms catalyze the reaction so that the reaction rate becomes biologically significant. For a more detailed discussion of oxygen radicals, see Troll and Wiesner, Ann. Rev. Pharm. Tox, 25:509–28, 1985. Thus, the presence of any of these oxygen species is considered undesirable. Yet the penultimate question remains unanswered: Why do some organisms, ostensibly similar and existing in a similar environment, exhibit tumorigenesis while others do not?

A partial answer to the dichotomy concerning the manifestation or lack thereof of cancer in a tumor bearing population or the converse proposition may be found, in part, by the natural biological processes of aerobic eukaryotic organisms. These organisms have developed various defenses to the toxic, oxygen intermediates. Cellular production of enzymes that catalytically scavenge these intermediates significantly reduce their impact upon the cell. Examples of these enzymes are superoxide dismutase (SOD), catalase, and peroxidase. Some of these enzymes function with cofactors such as vitamin E, glutathione, and ascorbate. Thus, a balance occurs wherein the concentration levels of oxygen reduction intermediates, e.g. oxygen radicals, are held in check by biologically produced and/or acquired substances. Nevertheless, knowledge of this mechanism baits the question: Does an organism reduce the concentration levels of oxygen radicals to reduce its susceptibility of tumor formation, or does it process these radicals differently to mitigate their genotoxic effect on DNA?

The questions posed above delineate the problems confronted by the inventor of the present invention. A method for identifying the cause of tumor formation or non-formation would identify the precursor condition which determined whether cancer would manifest or not. Identification of this condition would provide a diagnostician with two important pieces of information. First, if the condition were conducive to carcinogenesis, then an assessment of cancer risk could be made. Second, modification of the condition, i.e., inhibiting the undesired reaction(s) attendant thereto, could block or reverse the manifestation of cancer. This modification of the precursor condition would not necessarily decrease the presence of a tumor promotor, such as the hydroxyl radical .OH, but rather would prevent the formation of genotoxic DNA lesions.

SUMMARY OF THE INVENTION

The present invention identifies the precursor condition responsible for genotoxic DNA modifications and more specifically for cancer formation induced by oxygen radicals and provides methods for detection of genotoxic injury and cancer, risk assessment, and therapy. In broad terms the invention comprises obtaining a specimen from a subject; assaying the specimen to determine the cellular redox potential; and identifying an increased risk of genotoxic injury or presence thereof when the cellular redox potential favors an oxidative state or identifying a decreased risk of genotoxic injury or presence thereof when the cellular redox potential favors a reductive state. A more specific method is directed to cancer detection or risk assessment and comprises obtaining a specimen containing DNA from a test subject; isolating the DNA from the specimen; assaying for at least one modified nucleotide base derived via reductive pathways and for at least one modified nucleotide base derived via oxidative pathways; comparing the level of the at least one modified nucleotide base derived via reductive pathways which relates to a reductive state to the level of the at least one modified nucleotide base derived via oxidative pathways which relates to an oxidative state; and identifying a greater cancerous or precancerous risk when the oxidative state is favored over the reductive state. A modification of the preceding method provides for surrogate molecules exhibiting redox ambivalence during intermediate mesomeric stages to be introduced into the test subject, assayed for stabilized end products which represent the two states, and similarly comparing the propensity of the subject to favor an oxidative state or a reductive state.

By understanding the role that the cellular redox potential plays in genotoxic injury and cytotoxic injury, methods for modulating that potential so as to affect carcinogenesis, for example, are described. One method is directed to specifically modulating cells having a known attribute by covalently linking an effector molecule that causes the redox potential to favor reductively derived modified bases to a targeting molecule that is complimentary to the known attribute. Thus, administration of this therapeutic agent is targeted to only cells having the known attribute whose redox potential is to be modulated. In another method, carrier bodies are formed which contain the effector molecules. The membrane of the carrier bodies may have integral therein targeting molecules which cause the carrying bodies to become associated with known attributes such as receptor sites. Still other methods are described such as using activators to elicit expression of specific genes that alter the cellular redox potential and use of in vivo transfection of replacement enzymes.

A critical finding made by the inventor is that the cellular redox potential generally determines the type of effect that an oxygen radical, e.g., the .OH radical, has on cellular DNA: When the cellular redox potential favors oxidative pathways over reductive pathways, the .OH radical will likely form genotoxic DNA lesions as opposed to less damaging formations, thereby increasing the risk of cancer or indicating the presence thereof. Thus, by comparing the concentration levels of one or more species of reductively derived DNA lesion to one or more species of oxidatively derived DNA lesion, a meaningful determination can be made concerning the genotoxic or carcinogenic profile of the subject. A progressively greater likelihood of genotoxic injury or cancer exists when progressively greater levels of oxidatively derived DNA lesions and progressively lesser levels of reductively derived DNA lesions are observed. Consequently, while nucleotide bases modified by oxygen radicals or other modifying agents in general are indicative of oxidative stress or genotoxic environments, it is the cellular redox potential of the subject, as preferably observed through analysis of the various modified nucleotide bases, that determines the genotoxic profile of the subject. Hence, a determination of the cellular redox potential provides immediate information regarding the susceptibility of DNA to genotoxic, oxidative damage.

By interpreting data obtained from laboratory experiments, the inventor determined that certain statistically significant ratios between certain species of DNA base lesions provided a valid predictive tool for determining the origin of tissue—from a cancerous or non-cancerous specimen. Particularly, the ratio of concentrations of at least one ring-opened DNA base lesion to at least one hydroxyl adduct DNA base lesion was shown to be an accurate diagnostic predictor of the status of the specimen. An especially strong correlation for determining the status of a specimen existed when comparing the ratio of concentrations, taken to the $\log_{10}$, of all ring-opened lesions to all hydroxyl adducts where cancer or an increased risk thereof generally occurs when the $\log_{10}$ ratio is negative. Continued research later established a mechanism—cellular redox chemistry—which explained this statistical correlation.

As a consequence of this finding, modulation of the cellular redox potential to alter the susceptibility of DNA to genotoxic, oxidative damage via oxidative pathways is of great importance when desiring to reduce the susceptibility of a subject to genotoxic injury or carcinogenesis, or to stay or reverse cancerous growth. Because DNA is both a biomarker of the redox potential and a factor in carcinogenesis, effecting a change in the redox potential can be monitored by evaluating the ratio of DNA lesions formed by reductive pathways to DNA lesions formed by oxidative pathways, and similarly can provide prognostic information regarding the cancer profile. Thus, therapeutic programs can be initiated to alter the cellular redox potential for the purpose of decreasing the formation of DNA lesions formed by the oxidative pathway. Moreover, by monitoring for the presence of these DNA lesions, assessment of cancer risk can also be obtained.

Using this diagnostic and prognostic method, a method for tracking the efficacy of treatment directed to reducing the carcinogenic status of the subject can be carried out. In such a method, a subject is exposed to one or more chemical substances which modifies the cellular redox potential so as to favor reductive pathways over oxidative pathways, or causes/enhances naturally occurring processes to carry out the same. Progress of such a treatment can be assayed by monitoring the ratios of ring-opened molecules to hydroxyl adducts. This assay beneficially provides a direct indicator of the effectiveness of such a treatment.

BRIEF DESCRIPTION OF THE DRAWINGS

FIG. 10 shows a variety of organosulfur compounds for inducing the expression of glutathione S-transferase.

DETAILED DESCRIPTION OF THE INVENTION

Figure 1:
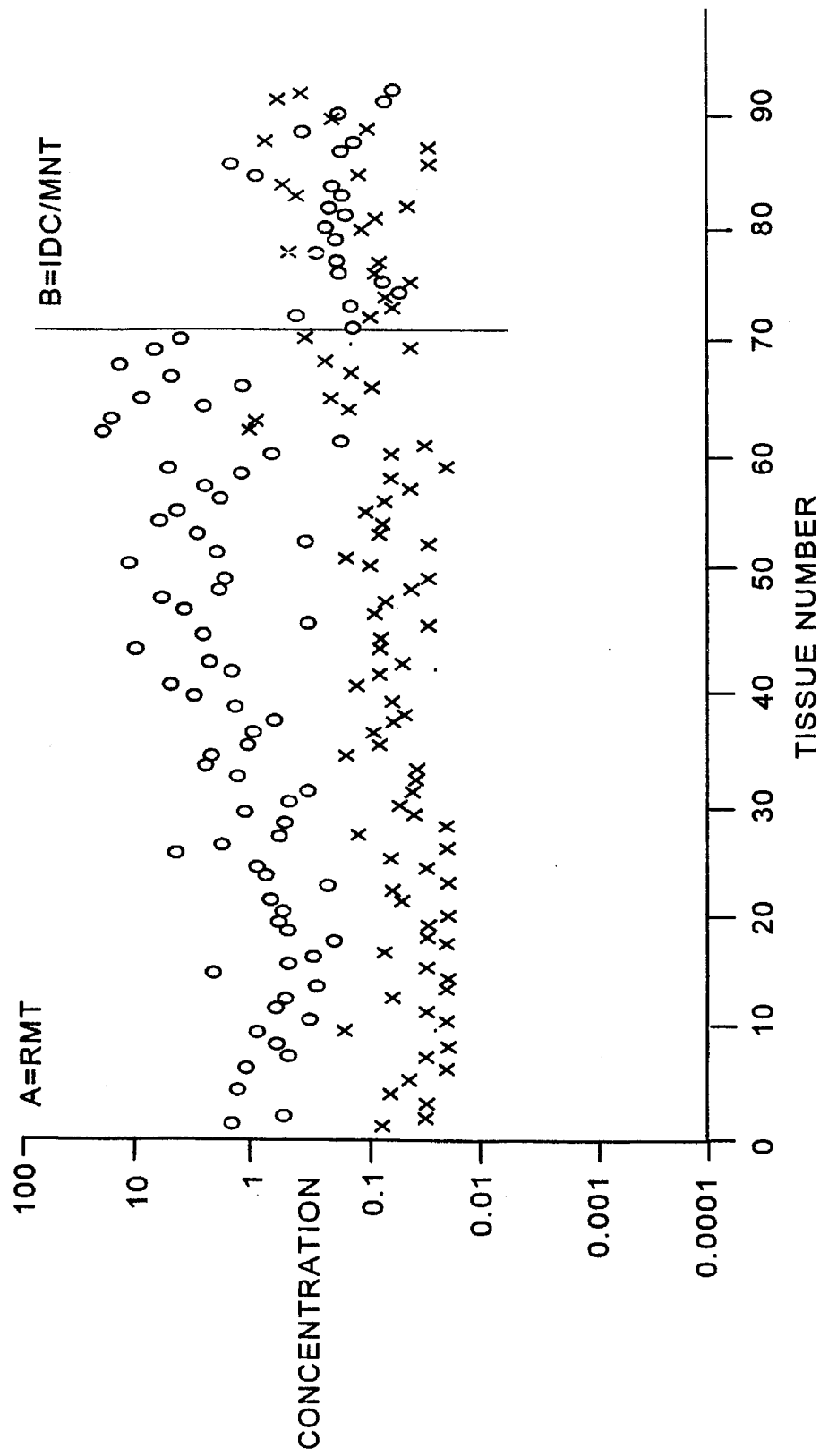
FIG. 1 is a scatterplot of the ratio between Fapy-A (shown as "O") and 8-OH-Gua (shown as "X") for cancerous and non-cancerous specimens.

The following example illustrates the important relationship between DNA that was reductively modified to form ring-opened lesions and DNA that was oxidatively modified to form hydroxyl adduct lesions for use as a diagnostic and prognostic tool to assess the cancer profile of a subject. The current example is directed towards tissue specimens obtained from the human breast of female subjects. However, because the analysis involves DNA, any specimen, be it for example, urine, fecal, serum, fluid, cell cultures, etc., would be suitable for analysis. Choosing a specimen for analysis is generally considered a design choice and is made in view of the type of screening to be conducted. Thus, tissue specimens may be most appropriate for analysis regarding cervical cancer screening and serum specimens may be most appropriate for leukemia screening.

As was previously discussed, hydroxyl radical-induced DNA base lesions, both ring-opened products such as 4,6-diamino-5-formamidopyrimidine (Fapy-A) and 2,6-diamino-4-hydroxy-5-formamidopyrimidine (Fapy-G), and 8-hydroxy derivatives such as 8-hydroxyguanine (8-OH-Gua) and 8-hydroxyadenine (8-OH-Ade) are products of cellular oxidative stress. High concentrations of a number of these lesions were initially found in naturally occurring cancers including invasive ductal carcinoma (IDC) of the female breast. In breast cancer, the base lesion concentrations were substantial, frequently representing greater than one base conversion in one thousand normal bases. Base lesions previously identified in IDC breast tissue included 8-OH-Gua, 8-OH-Ade, 5-hydroxymethyluracil (HMUra), Fapy-G, and to a much lesser degree, Fapy-A.

Further research revealed additional types of .OH-induced DNA lesions, such as 5-hydroxycytosine and 5-hydroxydantoin, which have been identified in a variety of cancerous human tissues. Collectively, these findings supported previously drawn conclusions with in vivo systems carried out by the inventor which suggested that .OH-induced modifications in the DNA bases, such as the addition of a single oxygen to the base structure, are a cause of mutagenesis and carcinogenesis. Thus, .OH-induced modifications of the DNA bases were considered to participate in carcinogenesis in a great variety of tissues.

The present research continued to investigate the role of radical-induced DNA modifications in genotoxic injury. However, it was desired to find a direct correlation between these modifications and the various stages of cancer beginning from normal, healthy test specimens to visually diseased test specimens. Hence, the first step was to obtain representative specimens of healthy, visually normal breast tissue; diseased but visually normal breast tissue; and visually diseased breast tissue. These specimens would then be assayed to determine the presence and level of various oxidatively modified nucleotide bases. From the obtained data, it was hoped that a meaningful relationship between the data and the specimens would then be generated so that a precursor condition could be identified. The results of the research are described in detail below.

DATA ACQUISITION

Reduction mammoplasty tissue (RMT) was obtained from 15 patients. The tissue from 10 patients was sequentially cut into 1 cm sagittal sections, 2 cm apart. Tissue from the remaining five RMT patients was divided into two sections. Two to 13 sections were obtained from each patient for a total of 70 samples. In addition, invasive ductal carcinomic tissue (IDC) and nearby microscopically normal tissue (MNT) were obtained from the cancerous breasts of 15 surgical patients. This group comprised 22 samples, seven of which were matched pairs (IDC-MNT); the remainder were single biopsy specimens from either IDC tissue or MNT. The RMT from the non-cancer patients was also microscopically normal with the exception of occasional incidence of non-neoplastic changes (e.g., fibrocystic). Neither the MNT nor the RMT showed evidence of inflammatory responses. Each of the IDC and MNT specimens had a mirror-image "control" histologic section prepared and examined in the absence of any knowledge of the DNA base lesion data.

After excision, each tissue was immediately frozen in liquid nitrogen and maintained at −70° C. The frozen tissue (~350 mg) was minced with a scalpel, placed in 3.0 ml of phosphate buffer solution and homogenized for one minute over ice. Then, 2.0 ml of 2X Lysis buffer (Applied Biosystems, Inc., Foster City, Calif.) and 300 µL of RNase A (Boehringer-Mannheim, Corp., Indianapolis, Ind.) were added and the sample was incubated at 60° C. for one hour. Proteinase K (Applied Biosystems, Inc.) was added and incubation was allowed to proceed overnight at 60° C. DNA was then extracted as previously described in U.S. patent application Ser. No. 07/806,487. The DNA was hydrolyzed using 60% formic acid which is not known to result in significant oxidation of nucleotide bases.

Trimethylsilyl (TMS) derivatives of the previously determined purine bases and HMUra were analyzed by Gas Chromatography-Mass Spectrometry with Selected Ion Monitoring (GC-MS/SIM) using a Hewlett-Packard Model 5890 microprocessor-controlled gas chromatograph interfaced to a Hewlett-Packard Model 5970B mass selective detector. The injector port and interface were both maintained at 260° C. The column was a fused silica capillary column (12.0 m; 0.2 mm inner diameter) coated with cross-linked 5% phenylmethylsilicone gum phase (film thickness, 0.33 µm). The column temperature was increased from 120° C. to 235° C. at 10° C./min. after initially being held for 2 min. at 120° C. Helium was used as the carrier gas with a flow through the column of 1 ml/min. The amount of TMS hydrolysate injected onto the column was 0.5 µg.

Quantitation of the DNA lesions was undertaken on the basis of the principal ion and confirmation of structure was undertaken by using qualifier ions. For example, the primary ion for the TMS derivative of Fapy-A was m/z=354 and the main qualifier ion was m/z=369. All analyses were performed in duplicate or triplicate, depending upon the amount of tissue available and the lipid content. About 350 mg of breast tissue, yielding an average of 150 µg of DNA, was usually sufficient for a base lesion analysis of a single sample in triplicate.

Fapy-A and the pyrimidine base, HMUra, were purchased from Sigma Chemical Co. and 8-OH-Gua was obtained from the Chemical Dynamics Corp. The 8-OH-Ade and Fapy-G were synthesized and purified using standard laboratory protocol and techniques.

The GC-MS/SIM analyses revealed dramatic differences in the concentration levels of the DNA base lesions between the cancerous breast tissue and the RMT. However, the data was not consistent. As hypothesized, the base lesion concentration levels of the IDC tissue and MNT specimens were remarkably different from that of the RMT. However, it was the differences in lesion profiles between the two that proved most intriguing. For example, both the IDC and the MNT were characterized on the one hand by relatively high concentrations of OH-adducts. The base lesions observed were 8-OH-Ade, 8-OH-Gua and HMUra. On the other hand, ring-opened (Fapy) derivatives were present in relatively small concentrations in the specimens derived from cancerous breasts. In the RMT, however, the relationship between the concentrations of the OH-adducts and Fapy derivatives was dramatically different—approaching inverse concentration levels in some instances. Thus, the base lesion profile (ring-opened derivatives versus OH adducts) provided the best distinguishing characteristic as between the cancerous and non-cancerous specimens.

To illustrate, attention is drawn to FIG. 1. FIG. 1 shows a scatterplot of the ratio between two representative products of radical attack. The tissue identification number is compared to its concentrations as obtained from analysis of DNA. Panel A is for the RMT and Panel B is for IDC tissue and MNT. The "O"s represent the ring-opened product Fapy-A; the "X"s represent the hydroxyl adduct 8-OH-Gua.

As is shown, Fapy-A concentrations predominate in the RMT sections compared to 8-OH-Gua by a factor of ~4- to 10-fold (Panel A). In fact, remarkably high concentrations of Fapy-A were found in the RMT (Mean=2.9±4.1 nMol/mg DNA; one base lesion in 320 normal bases). Surprisingly, for example, one patient had a RMT specimen that contained 21.0 nmol Fapy-A/mg DNA, or one base lesion in 46 normal bases (FIG. 1). This patient also had a relatively high 8-OH-Gua concentration of 1.1 nMol/mg DNA (one base lesion in 540 normal bases) which supports the proposition that high concentrations of Fapy derivatives in the RMT did not prevent the formation of significant concentrations of OH-adducts in some tissues. However, the high concentration level of Fapy derivatives may have acted to mitigate the genotoxic effect of the hydroxyl adducts. This matter will be discussed in more detail below. In contrast, the IDC and MNT sections were characterized overall by elevations in 8-OH-Gua compared to RMT, coupled with a marked depletion of Fapy-A residues (FIG. 1, Panel B).

From these observations, it was postulated that a condition existing in the test specimen or surrounding tissue promoted a mechanism that caused these differences to manifest. By finding such a precursor condition that caused these differences, it was believed that a valuable method for detecting the presence of cancer, and more importantly the likelihood of cancer, could be established.

STATISTICAL MODELS

In order to elucidate a condition, a statistically sound model would have to be used to transform the derived data into a useful form. Thus, the variables of the experiment were identified and a statistical analysis was performed. At least 22 different models were proposed and tested in order to find a reliable model which would provide the necessary relationship for establishing a method to detect and predict cancerous conditions.

To carry out this goal, suitable models would be able to predict the origin of the tissue sections, i.e., cancer or non-cancer, and would be able to determine the sensitivity and specificity of this classification. Sensitivity and specificity were defined in the usual way: sensitivity being the percentage of cancer tissue samples that were correctly classified (true positives) using the models, and specificity being the percentage of non-cancer tissue samples that were correctly classified (true negatives). The value $p<0.05$ was used to designate statistically significant differences and associations.

As a preliminary matter, an appropriate scale for comparing the data needed to be chosen. Graphical analysis showed that the logarithm of the data values produced results that were more closely related to cancer vs. non-cancer origin of tissue and more distributed than values on the natural scale. Thus, $\log_{10}$ concentrations and $\log_{10}$ ratios of concentrations were used in all model analyses.

The mean values for cancer and non-cancer tissue of the $\log_{10}$ concentrations and ratios, and the statistical significance of differences were calculated using methods developed by Laird and Ware that took into account the dependence of multiple sections from individual patients. The method is similar to ordinary multiple linear regression in other regards.

In order to build a model for predicting the origin of the tissue sections (cancer vs. non-cancer), the inventor used an extension of the aforementioned methods proposed by Stiratelli et al., which was developed for binary variables. As it pertained to the present research, it was a model for determining the probability that a specific tissue derived from a cancer or a non-cancer patient. The probability was expressed as a function of $\log_{10}$ concentrations or ratios of concentrations of oxidatively modified nucleotide bases. To use it as a predictive model, a cut-off probability, $P_c$, was required (e.g., $P_c$=0.5) and tissue samples with an estimated probability above this value were labeled as cancer-derived. The sensitivity and the specificity of the classification were calculated based on trial cut-off values from $P_c$=0.1 to $P_c$=0.9 in 0.1 increments, and the value of $P_c$ that gave the highest combined values (expressed as a sum) of sensitivity and specificity was then chosen.

As best shown in Table 1 below, a statistical analysis of these data yielded the mean values of the various indicators ($\log_{10}$ concentrations or $\log_{10}$ ratios of concentrations) for cancer and non-cancer tissue and the statistical significance of differences using the Laird-Ware regression model. The sensitivity and specificity were calculated using the predictive logistic regression model. Most significance levels were strikingly small, which indicated prominent differences between cancer and non-cancer tissue with respect to a wide array of predictors. Age was not included in the analysis, neither in the cancer dataset nor in the non-cancer dataset, and can be ruled out as a cause of the strong association.

TABLE 1

| Indicator | P-value* | Non-Cancer Patients Mean† | S.E. | Cancer Patients Mean† | S.E. | Predictive Model (Logistic Regression) Sensitivity (%) | Specificity (%) | P-value** |
|---|---|---|---|---|---|---|---|---|
| $\log_{10}$ (concentrations) | | | | | | | | |
| HMUra | .0000 | −3.3 | .1 | −2.8 | .1 | 91 | 69 | .0001 |
| Fapy-A | .0000 | .2 | .1 | −.7 | .1 | 82 | 93 | .0000 |
| 8-OH-Ade | .2 | −.6 | .1 | −.5 | .1 | 100 | 30 | .04 |
| Fapy-G | .01 | −1.4 | .1 | −1.7 | .1 | 55 | 90 | .01 |
| 8-OH-Gua | .04 | −1.2 | .1 | −.9 | .1 | 59 | 80 | .004 |
| Fapy-A + Fapy-G | .0000 | .3 | .1 | −.7 | .1 | 77 | 96 | .0000 |
| 8-OH-Ade + 8-OH-Gua | .2 | −.5 | .1 | −.3 | .1 | 100 | 36 | .02 |
| 8-OH-Ade + 8-OH-Gua + HMUra | .2 | −.5 | .1 | −.3 | .1 | 100 | 36 | .02 |
| $\log_{10}$ (ratio of concentrations) | | | | | | | | |
| Fapy-A/HMUra | .0000 | 3.6 | .1 | 2.0 | .1 | 91 | 97 | .0001 |
| 8-OH-Ade/HMUra | .001 | 2.7 | .1 | 2.3 | .1 | 91 | 44 | .004 |
| Fapy-G/HMUra | .0000 | 1.9 | .1 | 1.0 | .1 | 73 | 97 | .0000 |
| $\log_{10}$ (ratio of concentrations) | | | | | | | | |
| 8-OH-Gua/HMUra | .02 | 2.1 | .1 | 1.9 | .1 | 95 | 30 | .04 |
| Fapy-A/8-OH-Ade | .0000 | .9 | .1 | −.3 | .1 | 91 | 96 | .0000 |
| Fapy-A/Fapy-G | .0000 | 1.7 | .1 | 1.0 | .1 | 95 | 79 | .0000 |
| Fapy-A/8-OH-Gua | .0000 | 1.4 | .1 | .2 | .1 | 91 | 94 | .0001 |
| 8-OH-Ade/Fapy-G | .0004 | .8 | .1 | 1.3 | .1 | 68 | 91 | .0003 |
| 8-OH-Ade/8-OH-Gua | .06 | .6 | .03 | .4 | .1 | 64 | 63 | .09 |
| Fapy-G/8-OH-Gua | .0000 | −.2 | .1 | −.8 | .1 | 68 | 91 | .0002 |
| Fapy-A/(8-OH-Ade + 8-OH-Gua) | .0000 | .8 | .1 | −.4 | .1 | 91 | 97 | .0001 |
| Fapy-A/(8-OH-Ade + 8-OH-Gua + HMUra) | .0000 | .8 | .1 | −.4 | .1 | 91 | 97 | .0001 |
| (Fapy-A + Fapy-G)/ (8-OH-Ade + 8-OH-Gua) | .0000 | .8 | .1 | −.4 | .1 | 91 | 97 | .0000 |
| (Fapy-A + Fapy-G)/ (8-OH-Ade + 8-OH-Gua + HMUra) | .0000 | .8 | .1 | −.4 | .1 | 91 | 97 | .0000 |

*Based on linear regression random-effects model, testing the null hypothesis of equality of means for cancer and non-cancer (RMT) patients.
**Based on logistic regression random-effects model, testing the null hypothesis that the $\log_{10}$ value is not associated with cancer vs. non-cancer (RMT) classification of tissue section.
† Mean of the $\log_{10}$ values for the tissue specimens.

Figure 2:
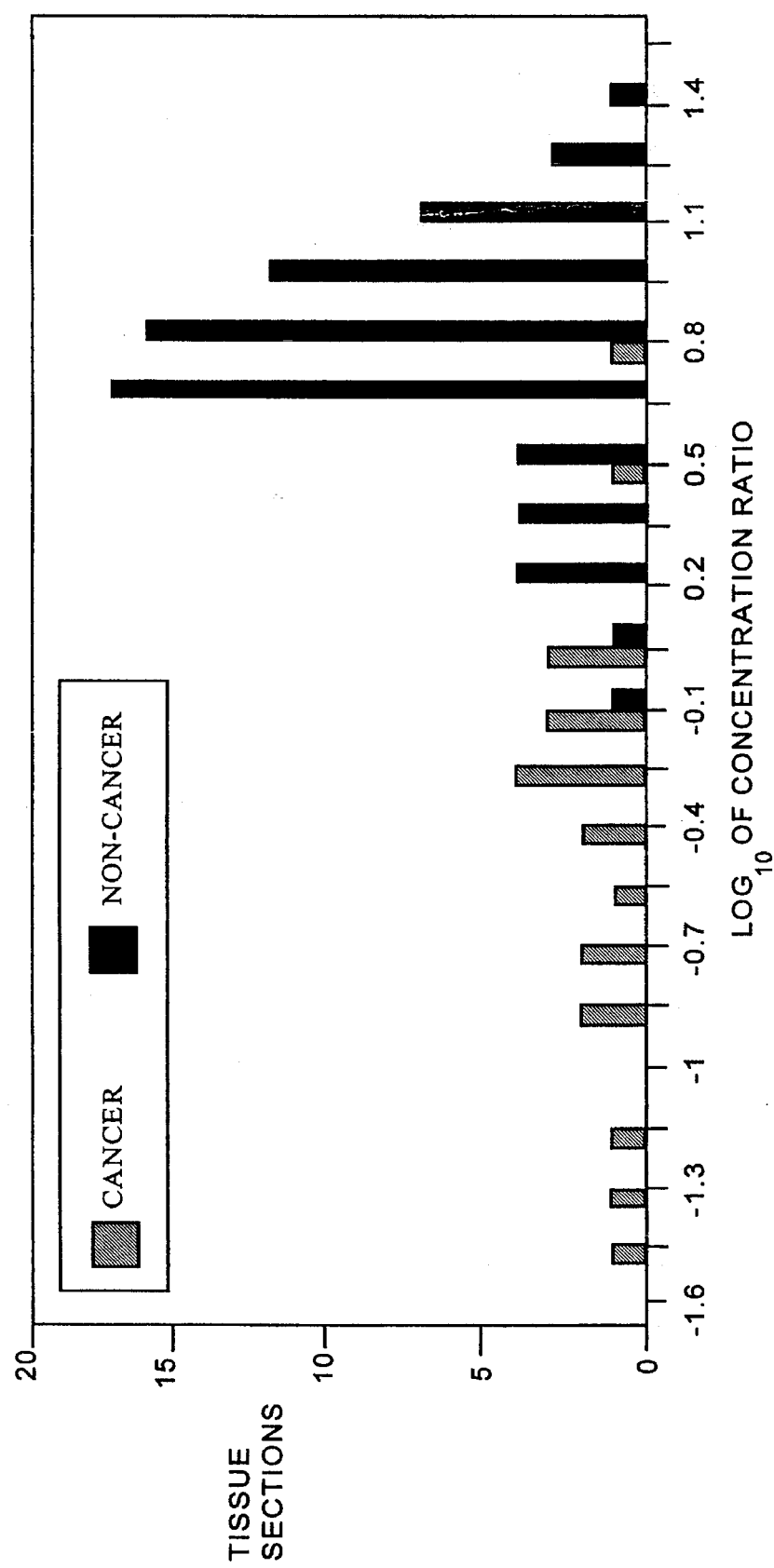
FIG. 2 is a histogram comparing the $\log_{10}$ concentration ratios of Fapy vs. 8-hydroxyl base lesions between data obtained from cancerous and non-cancerous specimens.

A graphical interpretation of these data is shown as a histogram in FIG. 2. Here, the total number of tissue sections having various $\log_{10}$ concentration ratios (Fapy versus 8-hydroxyl base lesions) are plotted. These results graphically indicate that fundamental differences exist in the base lesion profiles between cancerous and non-cancerous tissues. From this graph it can be seen that around $\log_{10} \leq 0$, a manifest cancerous state begins to appear with progressively increasing frequency.

Due to the number of comparisons made (22 predictors were assessed), it is likely that one or two would be statistically significant by chance alone. However, if all the p-values in Table 1 are multiplied by 22, which is the conservative Bonferroni adjustment, almost all of the p-values would still be statistically significant, including those for the $\log_{10}$ ratio that are considered further below.

The size of this dataset did not allow definitive selection among the several good models. The predictive equation was $\log_e [P/(1−P)]=0.76−6.34 \times \log_{10}$ (ratio) where P was the probability that a tissue sample derived from a cancer patient and "ratio" referred to the ratio of the sum of the two Fapy derivatives to the sum of the two OH-adducts plus HMUra.

The standard errors of the constant term and for the multiplier of the $\log_{10}$ ratio in the model above were 0.58 and 1.53, respectively. Using the model and the cut-off $P_c=0.5$, tissue samples with an estimated probability $P>0.5$ were classified as cancer-derived, and those with $P\leq 0.5$ were classified as non-cancer derived. The corresponding ratio of concentrations that best divided cancer from non-cancer samples was 1.32. As can be seen in Table 1, the sensitivity (91%) and specificity (97%) are both very high.

The accuracy of classification of tissue sections for each patient is shown in Table 2 below. In addition to the classification based on (Fapy-A+Fapy-G)/(8-OH-Ade+8-OH-Gua+HMUra), the classification based on a model of high sensitivity and specificity using the ratio (Fapy-A/8-OH-Gua) is also shown. In the latter model, the predictive equation was $\log_e [P/(1-P)]=3.71-5.51\times\log_{10}$ (ratio). The standard errors of the intercept and multiplier of $\log_{10}$ were 1.20 and 1.38, respectively. The cut-point for the predictive probability used in classifying a cancer-derived tissue was $P_c>0.4$ which corresponded to a ratio of concentrations of 5.6 or less.

TABLE 2

| Patient No., type of tissue | Classification of sections based on $\log_{10}$ (Fapy-A + Fapy-G/(8-OH-Ade + 8-OH-Gua + HMUra) N Incorrect/N total | Classification of sections based on $\log_{10}$ (Fapy-A)/(8-OH-Gua) N Incorrect/N total |
|---|---|---|
| 1, RMT | 0/7 | 0/7 |
| 2, RMT | 0/13 | 2/13 |
| 3, RMT | 0/4 | 1/4 |
| 4, RMT | 0/5 | 1/5 |
| 5, RMT | 1/5 | 0/5 |
| 6, RMT | 0/5 | 0/5 |
| 7, RMT | 0/5 | 0/5 |
| 8, RMT | 0/6 | 0/6 |
| 9, RMT | 0/5 | 0/5 |
| 10, RMT | 0/2 | 0/2 |
| 11, RMT | 0/2 | 0/2 |
| 12, RMT | 0/2 | 0/2 |
| 13, RMT | 0/2 | 0/2 |
| 14, RMT | 1/5 | 0/5 |
| 15, RMT | 0/2 | 0/2 |
| 16, cancer | 0/1 | 0/1 |
| 17, cancer | 0/1 | 0/1 |
| 18, cancer | 0/1 | 0/1 |
| 19, cancer | 0/1 | 0/1 |
| 20, cancer | 0/1 | 0/1 |
| 21, cancer | 0/1 | 0/1 |
| 22, cancer | 0/1 | 0/1 |
| 23, cancer | 0/1 | 0/1 |
| 24, cancer | 0/2** | 0/2** |
| 25, cancer | 0/2** | 0/2** |
| 26, cancer | 0/2** | 0/2** |
| 27, cancer | 2/2** | 2/2** |
| 28, cancer | 0/2** | 0/2** |
| 29, cancer | 0/2** | 0/2** |
| 30, cancer | 0/2** | 0/2** |
| TOTAL | 4/92 | 6/92 |

*Tissue was classified as derived from a cancer patient if ratio of concentrations $\log_{10}$ (Fapy-A + Fapy-G)/(8-OH-Ade + 8-OH-Gua + HMUra) was <1.32 (second column) or $\log_{10}$ (Fapy-A)/(8-OH-Gua) was <5.6 (third column).
**Represents paired IDC and MNT from the same patient.

The comparison of $\log_{10}$ concentrations and ratios between IDC and MNT showed no statistical differences. Note that because of the small sample size (22 sections), large differences in modified base concentrations or ratios between tumor and microscopically normal areas could not be ruled out.

PRECURSOR CONDITION FOR ASSESSING GENOTOXIC INJURY AND CANCER PROFILE

The foregoing statistical models provided the inventor with important information—an association existed between the base lesion profile of a specimen and its cancer status or risk thereof. Consequently, it was believed that the condition responsible for producing these distinctive, oxidatively modified, base signatures was the true precursor condition for determining whether radical attacks on DNA would lead to cancerous or non-cancerous tissue. By identifying the condition and knowing which type of oxidative modifications to DNA bases would be affected by the condition, an assay for the condition would provide a diagnostician with information concerning the cancer status or cancer risk of a subject.

Through diligent research, cellular redox potential was found to be the condition that explained the observed difference between lesion species. In vitro studies involving hydroxyl radical attacks on purine molecules revealed that the purine hydroxyl adduct was redox ambivalent. This meant that subsequent to a hydroxyl radical attack on a purine molecule, an intermediate or mesomeric purine radical was formed. This radical could then stabilize into one of two species of molecules—a ring-opened Fapy molecule if reductively stabilized, or a hydroxyl adduct molecule if oxidatively stabilized. The stabilized products of the in vitro purine experiments were similar to the observed base lesions of the previously described experiment. For a comprehensive discussion on in vitro redox chemistry and redox ambivalence, see Steenken S., Purine Bases, Nucleosides, and Nucleotides: Aqueous Solution Redox Chemistry and Transformation Reactions of Their Radical Cations and $e^-$ and OH Adducts, Chem. Rev. 1989; 89; 503–20. Thus, it was believed that the cellular redox potential of the breast tissue, either oxidative or reductive, would determine which species of stabilized DNA molecule would form and whether a genotoxic or potentially cytotoxic mutation of DNA would occur.

Figure 3:
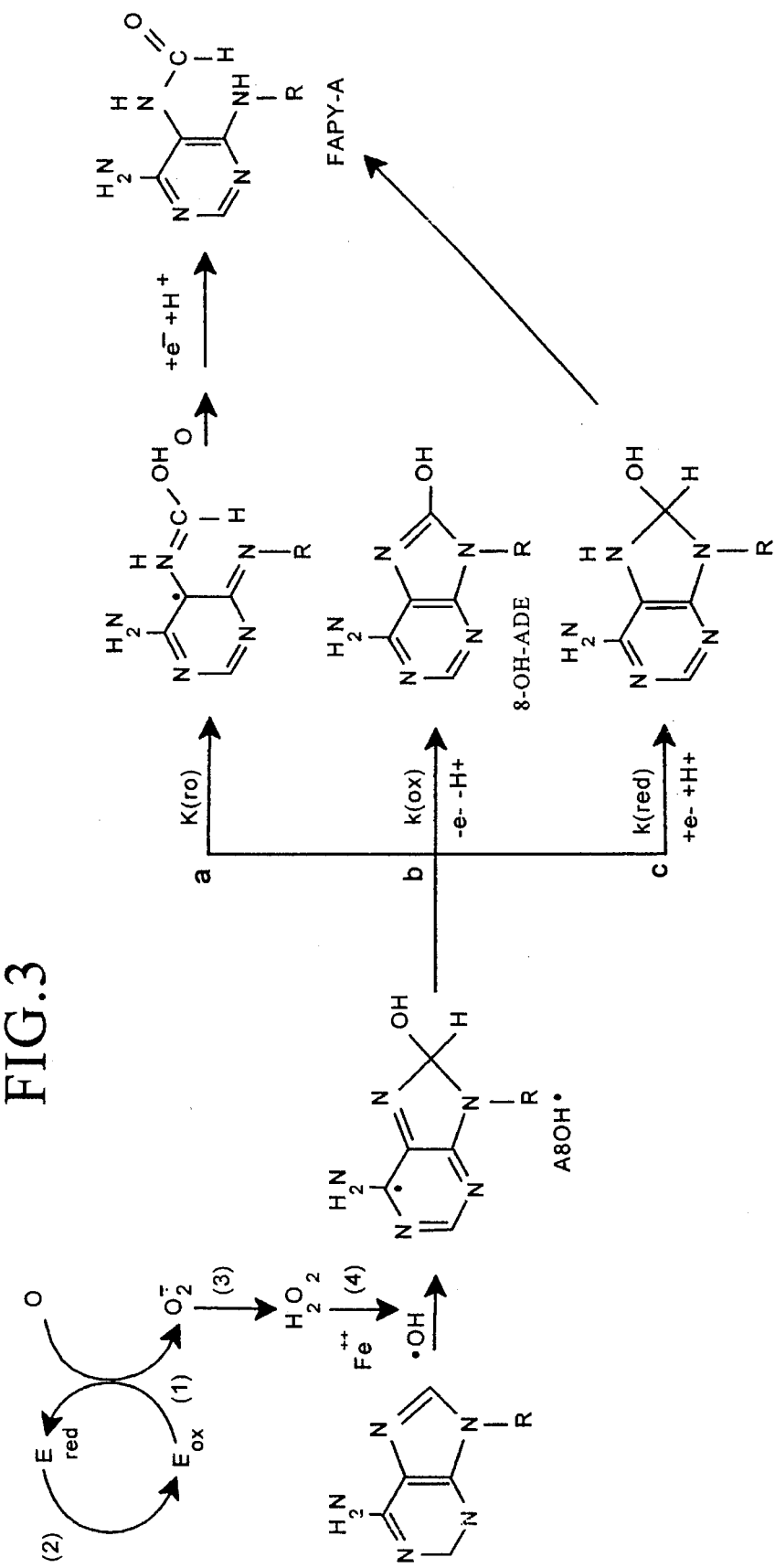
FIG. 3 is a proposed in vivo process for the production of and attack by hydroxyl radicals on DNA and subsequent stabilized end products derived via ring opening, oxidative, and reductive pathways.

FIG. 3 illustrates a proposed in vivo process whereby adenine, a purine base, is subject to attack by a hydroxyl radical produced during normal biological processes to yield a mesomeric purine hydroxyl radical—an 8-oxyl adduct of adenine (A8OH.). Depending upon cellular redox conditions, oxidative or reductive pathways are chosen. Ring-opening pathway (a) illustrates a unimolecular formation of a ring-opened molecule with subsequent electron loss and protonation. Oxidative pathway (b) illustrates the formation of a hydroxyl adduct molecule via a one electron oxidation and deprotonation. Reductive pathway (c) illustrates the formation of a ring-opened Fapy molecule via a one electron reduction and protonation with subsequent hydrolysis. It is believed that the intermediate hydrate should not be observed if reducing equivalents were not present. Support for this mechanism can be found in the fact that ring-opened Fapy molecules are significantly less abundant, in vitro, when small concentration of oxidants such as $O_2$ or $Fe(CN)_6^{3-}$ are present.

The redox ambivalence of the A8OH. radical can be explained by the reactions that take place during the formation of the hydroxyl adducts and ring-opened products. Because the ring-opening process is unimolecular, it can compete efficiently with the bimolecular oxidation and reduction of the A8OH. radical: For an environment that had equal concentrations of oxidants and reductants, the reaction products, i.e. 8-OH-Ade and Fapy-A, appear in equal concentrations. In vitro experiments also confirm that guanine behaves in a similar manner because it too, is a derivative of the purine molecule and exhibits redox ambivalence.

Thus, cellular redox condition as it relates to the derivation of the various species of modified nucleotide bases provided the best fit for the statistically derived models. Not surprisingly, the $\log_{10}$ ratio of summed Fapy derivatives to summed OH-adducts proved to be the best predictor of tissue origin. As Table 1 clearly shows, however, there are other models with high sensitivity and specificity and very small significance levels. It should be noted, though, that those models with the highest sensitivity and specificity all involve the comparison of one pathway—reductive, to the other pathway—oxidative.

Figure 4:
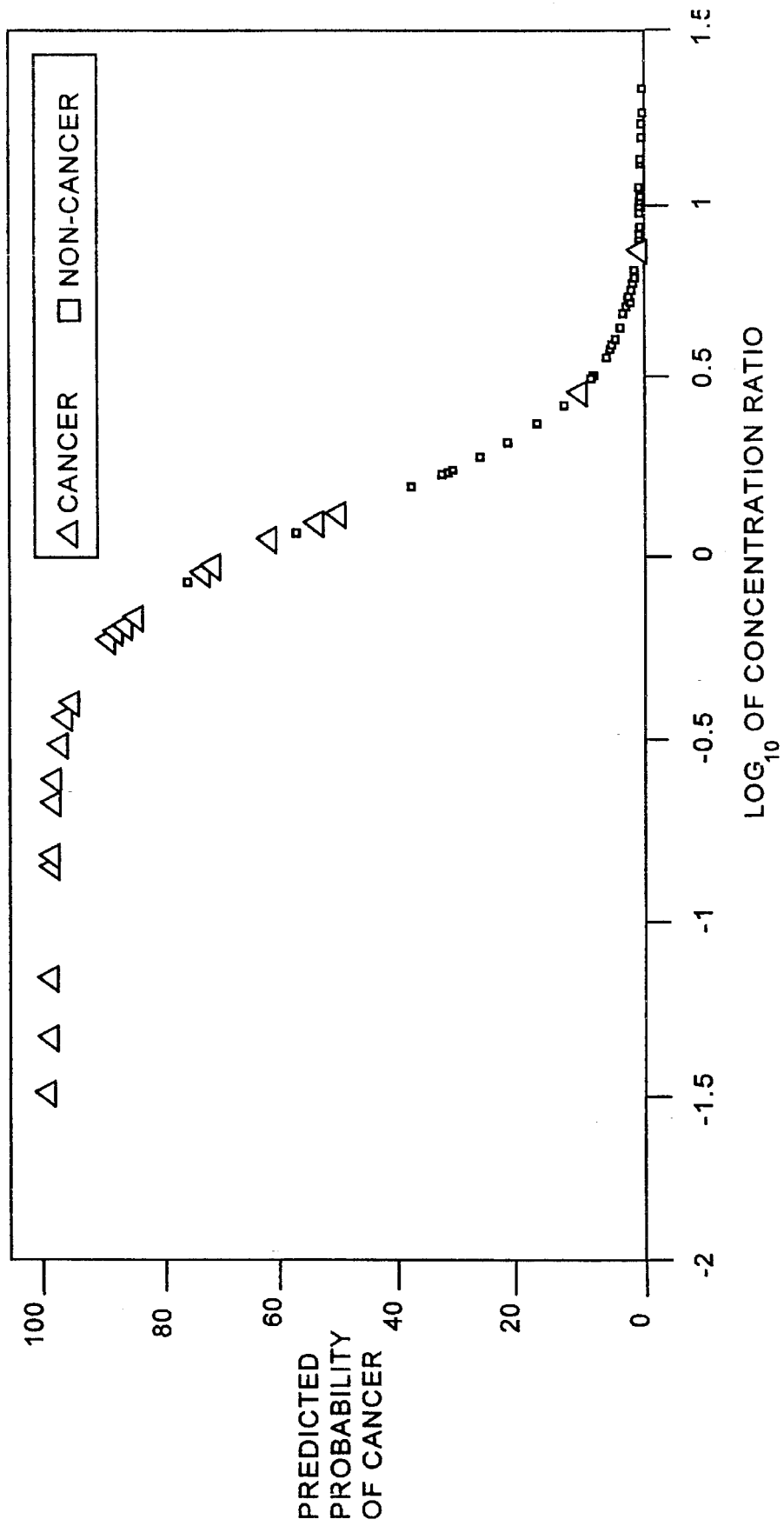
FIG. 4 is a plot of the obtained data illustrating the strong associative and predictive abilities of the models for determining a risk factor for manifesting cancer.

Based upon the statistically significant differences in base lesion profiles (modified base concentration levels) between the cancer and normal tissue, which were consistent with known biological mechanisms, a graph of predicted probability of the cancerous origin of a tissue vs. $\log_{10}$ of the concentration ratios was constructed. FIG. 4 plots the collected data and demonstrates the strong ability of this model to discern the status of each tissue. By utilizing this model and knowledge of the condition and related mechanisms which cause the selection of one stabilization pathway over another, an accurate determination can be made as to the cancer profile of a subject based upon an analysis of a test specimen obtained therefrom.

It is also important to realize the role that the hydroxyl adducts and the Fapy derivative play in DNA replication. As was stated earlier, hydroxyl adducts are genotoxic, i.e., they significantly promote DNA misreplication, while Fapy derivatives are putatively cytotoxic, i.e. they block DNA synthesis instead of promoting misreplication. Consequently, high levels of Fapy derivatives stay DNA synthesis, either beneficial or detrimental. The implication is that Fapy derivatives generally mitigate the genotoxic effect of hydroxyl adducts which may be present with the Fapy derivatives subsequent to a oxygen radical attack on DNA. Thus, a decrease in Fapy derivative concentrations with an increase in hydroxyl adduct concentrations further enhances the propensity for cancer, either manifested or potential, of cells exhibiting these base lesion profiles.

MEASUREMENT OF CELLULAR REDOX POTENTIAL

There are currently many different methods to measure cellular redox potential. Examples include flow cytometric techniques, fluorescence assays, phosphorescence measurement, enzyme measurements, electron spin resonance spectrometric measurements, etc. But in the context of determining the cellular redox potential as it is now known to relate to genotoxicity in general and to carcinogenesis in particular, determination of this potential by directly analyzing the condition of DNA is believed to provide the most comprehensive means for assessment. The reason for this being that DNA is not only an excellent biomarker of redox conditions in that it has redox ambivalent molecules, but it is also responsible for cellular replication or misreplication. Thus, the cellular redox potential of a specimen can be determined by DNA analysis and its impact on genotoxic injury or carcinogenesis directly observed.

The foregoing discussion shows the desirability of determining the cellular redox potential by DNA analysis. However, it may be desirable to use a different biomarker or surrogate do make this determination. Such a marker or surrogate would be functionally similar to DNA so as to most accurately mimic the DNA's redox ambivalence subsequent to an oxygen radical attack, thus maintaining its beneficial attributes as discussed above. A benefit of using a surrogate is in its ability to migrate throughout a test subject, if so desired, so as to give a broader picture of the redox potential of the subject. Another benefit is that the surrogate can be "tagged" to make isolation and identification more easy. Thus, only tagged molecules would be analyzed to determine the redox potential of a test subject or specimen. As such, less complex and expensive means for analyzing the compound could be utilized.

An example of such a surrogate would be a 3-deoxyribose derivative of guanine or uridine (as opposed to the normal 2-deoxyribose derivative). 3-deoxyribose and related analogs can be obtained from Sigma Chemical, St. Louis Mo. Ideally, the surrogate would have a base structure containing $^{13}C$ to simplify isolation during the analysis process. Because this compound is essentially an isomer of the naturally occurring 2-deoxyribose derivatives, it is not involved in DNA synthesis and therefore would be more easily isolated from a specimen. And because the surrogate is nearly identical to biologically produced derivative, biological incompatibility or toxicity is minimized. The surrogate could be introduced via intravenous injection or by liposomes as discussed in detail below. The surrogate compound then can be obtained from fluid of the test subject. Isolation of the surrogate can be made using GC/MS equipment or other equipment suitable for this surrogate.

INTERVENTION OF CELLULAR REDOX POTENTIAL TO DISCOURAGE PRODUCTION OF MODIFIED NUCLEOTIDE BASES DERIVED VIA OXIDATIVE PATHWAYS

From the foregoing discussions it can be seen that modulating the cellular redox potential would affect the species of DNA base lesions formed subsequent to an oxidative attack on the DNA. More specifically, by administering one or more chemical substances that directly or indirectly discourage or repress the formation of modified bases derived via the oxidative pathway, the likelihood of genotoxic injury in general and carcinogenesis in particular would be decreased. Such chemical substances (effector molecules) include reductants such as reduced glutathione (GSH), reduced nicotinamide adenine dinucleotide (NADH), reduced flavin adenine dinucleotide ($FADH_2$), or reduced nicotinamide adenine diphosphate (NADPH); scavengers such as alkene bonds, nucleotide bases, or salicylic acid; radical traps such as N-O spin traps; or iron chelators such as transferrin, ferritin, or imminodiacetic acid. Chemical substance which indirectly cause reductive stabilization of redox ambivalent molecules include activators of expression in genes encoding in situ modulators of DNA repair, $H_2O_2$ degradation, or free radical detoxifying enzymes such as SOD, catalase, P-450 reductase, glutathione peroxidase, and DT-diaphorase.

The common factor of the above identified effector molecules is that each works directly or indirectly to cause redox ambivalent molecules, e.g. mesomeric purine radicals, to stabilize via reductive pathways. This modulation of the redox potential is directed not specifically towards the elimination or reduction of, for example, hydroxyl radicals. Instead, the primary goal is to create cellular conditions wherein modifications to DNA bases will follow reductive pathways to form, for example, Fapy molecules. Beneficially, these compounds may also reduce the concentration levels of radical producing reagents.

With the knowledge that reductive pathways are essentially equal to or are favored over oxidative pathways in healthy specimens when discussing DNA base lesions, and that a plethora of means may be available for altering cellular redox potential, it can be seen that numerous and diverse methods may exist for decreasing the concentration levels of base lesions derived via oxidative pathways. Consequently, it would be impractical to identify all possible means for effecting the desired change. The following are examples of procedures that would enable a person skilled in the art to carry out the modulation of cellular redox potential for specific cells, thereby enabling the modulation of cellular redox potential of specific sites either suspected of being especially susceptible to or already exhibiting carcinogenesis. For purposes of these examples, breast epithelial cells have been chosen, although it is to be understood that any cell involved in potentially carcinogenic transformation can be chosen as a target.

EXAMPLE 1: USE OF EFFECTOR MOLECULES COVALENTLY LINKED WITH TARGETING MOLECULES

Initially, a targeting molecule must be identified. The targeting molecule is considered a molecule whose receptor is expressed by and is associated with a particular cell or cells where the redox potential of those cell(s) is to be modulated in accordance with the methods set forth below. If the cellular redox potential of the breast is to be modulated, then breast epithelial cells may be chosen. These cells have highly expressed receptors for estrogen. Therefore, because receptors for estrogen (the targeting molecule) are highly expressed on breast epithelial cells, an effector molecule associated with estrogen will interact with the desired cell type.

Figure 5:
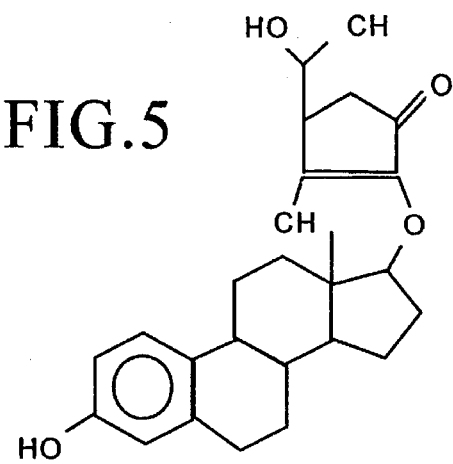
FIG. 5 is a structural representation of an ascorbic acid moiety coupled with estradiol for use in modulating the cellular redox potential of breast epithelial cells.
Figure 6:
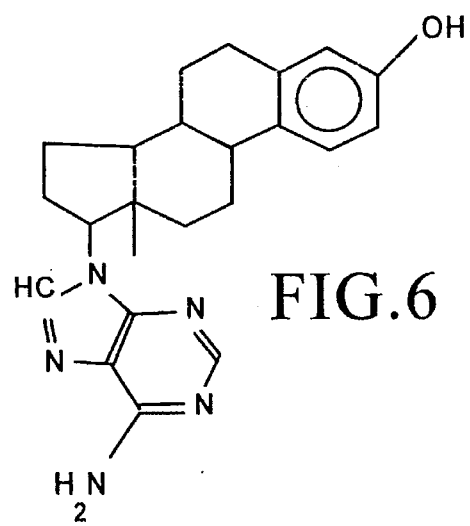
FIG. 6 is a structural representation of an adenine moiety coupled with estradiol for use in modulating the cellular redox potential of breast epithelial cells.
Figure 7:
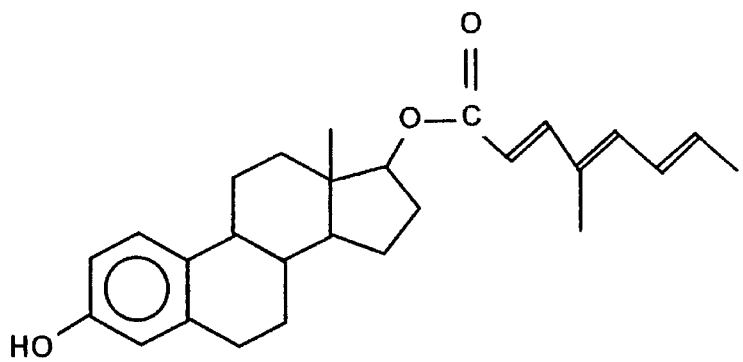
FIG. 7 is a structural representation of a conjugated double bond moiety coupled with estradiol for use in modulating the cellular redox potential of breast epithelial cells.
Figure 8:
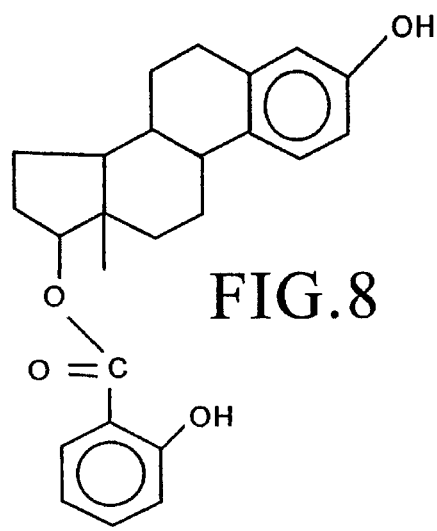
FIG. 8 is a structural representation of a salicylic acid moiety coupled with estradiol for use in modulating the cellular redox potential of breast epithelial cells.
Figure 9:
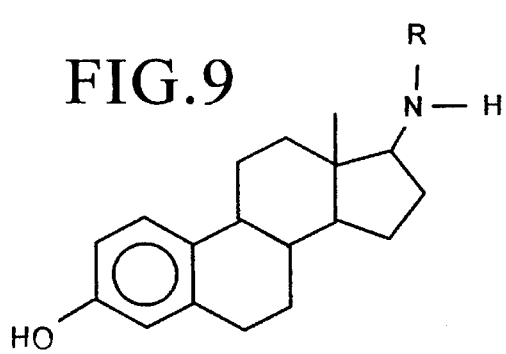
FIG. 9 is a structural representation of an ε-amino group of lysine or an α-amino acid residue couple with estradiol (R) or to a low molecular weight component having functional groups which act as reductants, scavengers, spin traps, metal ion chelators, etc. for modulating the cellular redox potential of breast epithelial cells.

An appropriate therapeutic agent might, for example, combine an effector molecule, such as an ascorbic acid moiety, with the targeting molecule estrogen by covalent linkage means. Such an agent may be prepared by conventional means such as by utilizing the Williamson synthesis (a nucleophilic substitution of an alkoxide ion for a halide ion thereby creating a stable ether linkage between the 17-hydroxyl group of estrogen and a hydroxyl group of ascorbic acid). The resulting therapeutic agent is shown in FIG. 5. Another example of this type of targeting delivery mechanism is shown in FIG. 6. Here, the 17-keto group of estrone can be linked to a different effector molecule, a primary amino group of the DNA nucleoside adenine. Further examples of this type of delivery mechanism are shown in FIGS. 7, 8, and 9.

EXAMPLE 2: USE OF EFFECTOR MOLECULES WITHIN CARRIER BODIES

Another type of delivery mechanism uses carrier bodies having a degradable membrane which contain the previously discussed effector molecules. Bonded to the exterior membrane of the bodies might be an appropriate targeting group such as estrogen, if targeting is desired; else the exterior membrane would generally be nonspecific and infiltrate throughout the subject. If the later option is chosen, carrier bodies having variably degradable membranes can be used in order to temporally vary the level of effector concentrations. In this manner, the subject would not be subject to a concentration "spike." Either variable density membranes or membranes only degradable by certain enzymes, for example, could be used.

In a preferred form, liposomes comprise the carrier body. If it is desired to include a targeting group with the liposome, such a carrier body can be accomplished by introducing estrogen into the phosphatidic acid mixture during liposome formation. The estrogen would then link to the phosphate of phosphatidic acid via its 17-hydroxyl group. Internal to the liposome would be the appropriate effector molecules. By introducing a soluble effector containing solution into the phospholipid-saline solution mixture during liposome formation, the aqueous matter surrounded by the lipid membrane would contain the desired effector. In addition to the introduction means identified below, the liposomes can be delivered directly to the targeted area by injection. Subsequent degradation and/or metabolic destruction of the lipid membrane would release the effector molecules.

The foregoing therapeutic agents described in Examples 1 and 2 can be introduced into a human subject via oral or intravenous methods to modulate the redox conditions in breast epithelial cells. Dosage requirements for these agents can be determined in accordance with the protocol established for drugs such as isotretinoin which was described in Lippman, T., et al., Comparison of Low-Dose Isotretinoin with Beta Carotene to Prevent Oral Carcinogensis, N Engl J Med, 1993;328:15–20. In this paper, an initial dose of isotrentinoin of 1.5 mg/kg of body weight per day was administered for a three month period to human test subjects exhibiting leukoplakia (a premalignant lesion of the epithelium of the oral cavity). In the second phase, the dosage level was reduced to 0.5 mg/kg per day and continued for nine months. Favorable responses or stabilization of the lesion(s) were reported and only mild toxicity responses were observed. Additional guidance can be found in Rutqvist, L., et al., J. Natl. Cancer Inst., 1991, 83:1299–1306; Fornander, T., et al., J. Clin. Oncol., 1990, 8:1019–24; Bagdade, J., et al., J Clin. Endocrinol. & Metab., 1990, 70:1132–35. In these papers, dosage amounts varied from between 10 mg per person per day to 40 mg per person per day yielding beneficial results and minimal side effects. The afore referenced research documents are believed to illustrate the skill in the art and are incorporated herein by reference. The therapeutic effect should be observed within 3 to 6 months from the beginning of treatment. Depending upon the subject's propensity to favor oxidative pathways as determined by analysis of the redox condition, a continual low level treatment may be necessary and in many instances, desirable. Such a determination can only be made on a case by case basis.

EXAMPLE 3: USE OF ACTIVATORS FOR ELICITING EXPRESSION OF SPECIFIC GENES

Based upon current knowledge, alternate means for modulating cellular redox potential exist. These alternate means include eliciting the expression of enzymes which act in detoxifying, repairing of DNA, or increasing reducing power reactions. Thus, introduction of activators of expression of such enzymes would include activators of expression of genes encoding in situ modulators of DNA repair, hydrogen peroxide degradation, or free radical detoxifying enzymes (enzymes such as superoxide dismutase, catalase, cytochrome P-450 oxidase and reductase, glutathione S-transferase, transferrin, ferritin, glutathione peroxidase, xanthene oxidase, or DT-diaphorase). For example, FIG. 10 illustrates various compounds which would elicit the expression of glutathione S-transferase (a prominent biochemical system which reduces concentration levels of hydroxyl radicals). These organosulfur compounds have been shown to induce glutathione S-transferase activity in the mouse. For a discussion of various means for eliciting the expression of genes encoding such enzymes or activities, see generally Temin, H. M., in Gene Transfer, pp. 149–87, Plenum Press, New York, 1986; Current Protocols in Molecular Biology, ed. by Ausubel, et al., John Wiley & Sons, New York, (1989) which are illustrative of the skill in the art in this field and are incorporated herein by reference.

Relevant dosages of such activators for therapeutic applications vary widely depending upon the activator and the test subject. Dosage amounts are generally effective in inducing glutathione S-transferase when administered orally in the amount of 7–21 mg/kg. See Maurya, A. and Singh, S., Differential Induction of Glutathione Transferase Isoenzymes of Mice Stomach by Diallyl Sulfide, a Naturally Occurring Anticarcinogen, 1991, Cancer Letters 57:121–29. Under these guidelines and protocols, it is expected that biologically relevant results would appear within days. For other activators, sufficient guidance to allow a person skilled in the art to determine dosage amounts can be found in Denda, A., et al., Carcinogenesis, 1993, 14:95–101. The foregoing references are believed to establish the state of the art in this respect.

EXAMPLE 4: USE OF IN VIVO TRANSFECTION OF REPLACEMENT ENZYMES

Yet another alternate method for modulating the cellular redox potential exists by utilizing in vivo transfection of "replacement" enzymes in targeted cells due to mutational damage to or lack of expression of endogenous genes. Such a method may be carried out by inserting cDNA coding for the appropriate genes (such as those genes identified in Example 3, above) in retroviral vectors and allowing them to be expressed in vivo, or inserted in cells in vitro and transplanting such cells into the subject. See generally Temin, H. M., Gene Transfer, pp. 149–87, Plenum Press, New York (1986), which is incorporated herein by reference as illustrative of the skill in the art. Cloning of the desired gene(s) may be carried out by using methods known and used by those persons skilled in the art.

Preparation of cDNA for a given enzyme can be prepared based upon the gene DNA sequence. The sequence data can be determined using standard techniques. See Current Protocols in Molecular Biology, supra.

The efficacy of any therapy can be judged by administering a desired means to cause a reduced cellular redox state to occur, and monitoring it's effect by analyzing DNA base lesions or suitable analogs that exhibit redox ambivalence. By periodically conducting a DNA base lesion profile, suitable analog profiles, or any other method for determining the cellular redox potential of a test specimen containing the targeted cells, a determination as to the relative success of the treatment, as measured by comparing the reductively versus oxidatively derived products, could be obtained and/or monitored.

INDUSTRIAL APPLICABILITY

The present invention will find special utility in the fields of cancer research, clinical practice, and therapy. The methods disclosed and claimed herein will permit rapid and accurate diagnosis of genotoxic injury including cancerous and precancerous conditions, or cancer risk, and will permit therapy directed to reducing the risk of cancer, or treating established cancer and monitoring the progress thereof.

What is claimed is:

1. A method for inducing a reductive cellular redox potential in a targeted cell group having DNA and monitoring the same comprising the steps of:
   a) introducing a gene expression activator into said targeted cells wherein the gene is induced to increase its expression and further wherein said gene encodes a free radical detoxifying enzyme;
   b) obtaining a test specimen from the test subject known to have the targeted cells;
   c) assaying the DNA associated with said test specimen for concentration levels of at least one ring-opened derivative and for at least one hydroxyl adduct; and
   d) comparing the concentration level of the at least one ring-opened derivative to the concentration level of the at least one hydroxyl adduct, wherein a reductive cellular redox potential exists when formation of ring-opened derivatives are favored over hydroxyl adducts.

2. A method for inducing a reductive cellular redox potential of a targeted cell group and monitoring the same comprising the steps of:
   a) determining the gene sequence for a free radical detoxifying enzyme;
   b) preparing and cloning cDNA based upon the gene sequence;
   c) introducing the cDNA into a test subject wherein the free radical detoxifying enzyme is expressed from said cDNA;
   d) obtaining a test specimen from the test subject known to have been exposed to the cDNA;
   e) assaying the DNA associated with said test specimen for concentration levels of at least one ring-opened derivative and for at least one hydroxyl adduct; and
   f) comparing the concentration level of the at least one ring-opened derivative to the concentration level of the at least one hydroxyl adduct, wherein a reductive cellular redox potential exists when formation of ring-opened derivatives are favored over hydroxyl adducts.

3. The method of claim 2 wherein the cDNA is inserted into retroviral vectors which are introduced into the test subject.

4. A method for determining a genotoxic cellular state in a tissue or fluid type having a plurality of cells with DNA comprising the steps of:
   a) identifying a test specimen representative of the plurality of cells;
   b) assaying the test specimen to determine its cellular redox potential; and
   c) determining a genotoxic cellular state in the tissue or fluid type when the cellular redox potential favors oxidative redox reaction pathways or determining a non-genotoxic cellular state in the tissue or fluid type when the cellular redox potential favors reductive redox reaction pathways.

5. The method of claim 4 wherein assaying the specimen in step b) comprises the step of:
   assaying for at least one modified nucleotide base derived via oxidative redox reaction pathways wherein the at least one base is a hydroxyl adduct of a DNA base.

6. The method of claim 5 wherein the hydroxyl adduct of a DNA base is selected from the group consisting of 8-hydroxyguanine (8-OH-Gua), 8-hydroxyadenine (8-OH-Ade), 5-hydroxymethyluracil (HMUra), 5-hydroxycytosine, and 5-hydroxydantoin.

7. The method of claim 4 wherein assaying the specimen in step b) comprises the step of:

assaying for at least one modified nucleotide base derived via reductive redox reaction pathways wherein the at least one base is a ring-opened derivative of a DNA base.

8. The method of claim 7 wherein the ring-opened derivative of a DNA base is selected from the group consisting of 4,6-diamino-5-formamidopyrimidine (Fapy-A) and 2,6-diamino-4-hydroxy-5-formamidopyrimidine (Fapy-G).

9. The method of claim 4 wherein assaying the specimen in step b) further comprises the step of:

assaying for at least one modified nucleotide base derived via oxidative redox reactive pathways wherein the at least one base is a hydroxyl adduct of a DNA base, and assaying for at least one modified nucleotide base derived via reductive redox reaction pathways wherein the at least one base is a ring-opened derivative.

10. The method of claim 9 wherein the hydroxyl adduct of a DNA bases is selected from the group consisting of 8-hydroxyguanine (8-OH-Gua), 8-hydroxyadenine (8-OH-Ade), 5-hydroxymethyluracil (HMUra), 5-hydroxycytosine, and 5-hydroxydantoin, and the ring-opened derivative of a DNA bases is selected from the group consisting of 4,6-diamino-5-formamidopyrimidine (Fapy-A) and 2,6-diamino-4-hydroxy-5-formamidopyrimidine (Fapy-G).

11. The method of claim 9 wherein an oxidative cellular redox reaction pathway is favored when the $\log_{10}$ ratio of concentrations of ring-opened derivatives versus hydroxyl adducts is substantially equal to or less than 0.5 and wherein the ring-opened derivatives comprise 4,6-diamino-5-formamidopyrimidine (Fapy-A) and 2,6-diamino-4-hydroxy-5-formamidopyrimidine (Fapy-G), and the hydroxyl adducts comprise 8-hydroxyguanine (8-OH-Gua), 8-hydroxyadenine (8-OH-Ade), and 5-hydroxymethyluracil (HMUra).

12. The method of claim 9 wherein an oxidative cellular redox reaction pathway is favored when the $\log_{10}$ ratio of concentrations of the at least one ring-opened derivative versus the at least one hydroxyl adduct is substantially equal to or less than zero (0).

13. A method for monitoring the efficacy of a cellular redox modulation regimen comprising the steps of:

a) initiating a cellular redox potential modulation regimen directed to a tissue or fluid type including a plurality of cells having DNA wherein the regimen is intended to promote a reductive cellular redox potential therein;

b) identifying a test specimen having said plurality of cells;

c) assaying the DNA of the test specimen to determine the level of at least one hydroxyl adduct thereof derived via oxidative redox reaction pathways and the level of at least one ring-opened derivative derived via reductive redox reaction pathways to create a first ratio of derivatives versus adducts;

d) repeating steps b) and c) to obtain a second ratio of derivatives versus adducts; and e) determining a shift towards a reductive cellular redox potential if the value of the second ratio is greater than the first ratio.

14. A method for determining the cellular redox potential of a specimen comprising a plurality of cells having DNA, said cells representative of a tissue or fluid type, the method comprising the steps of:

a) identifying a test specimen having said plurality of cells;

b) assaying the DNA of the test specimen to obtain concentration levels for at least one modified nucleotide base derived via oxidative pathways wherein the at least one base is a hydroxyl adduct of a DNA base and for at least one modified nucleotide base derived via reductive pathways wherein the at least one base is a ring-opened derivative; and c) identifying an oxidative cellular redox potential in the specimen when the concentration level of the at least one modified base derived via oxidative pathways is greater than the concentration level of the at least one base derived via reductive pathways.

15. The method of claim 14 wherein the hydroxyl adduct of a DNA bases is selected from the group consisting of 8-hydroxyguanine (8-OH-Gua), 8-hydroxyadenine (8-OH-Ade), 5-hydroxymethyluracil (HMUra), 5-hydroxycytosine, and 5-hydroxydantoin, and the ring-opened derivative of a DNA bases is selected from the group consisting of 4,6-diamino-5-formamidopyrimidine (Fapy-A) and 2,6-diamino-4-hydroxy-5-formamidopyrimidine (Fapy-G).

16. The method of claim 13 further comprising obtaining the $\log_{10}$ of the first ratio and the $\log_{10}$ of the second ratio wherein in step e), a shift towards a reductive cellular redox potential occurs when the $\log_{10}$ of the second ratio is greater than the $\log_{10}$ of the first ratio.

* * * * *